United States Patent [19]

Cragoe, Jr. et al.

[11] Patent Number: 4,775,695
[45] Date of Patent: Oct. 4, 1988

[54] SUBSTITUTED AMIDINOALKOXY AND AMIDINOALKYLAMINO INDANONES AND SALTS THEREOF

[75] Inventors: Edward J. Cragoe, Jr., Lansdale; Otto W. Woltersdorf, Jr., Chalfont, both of Pa.

[73] Assignee: Merck & Co., Inc., Rahway, N.J.

[21] Appl. No.: 56,842

[22] Filed: Jun. 1, 1987

[51] Int. Cl.$^4$ ........................................... A61K 31/155
[52] U.S. Cl. ..................................... 514/637; 564/246; 564/247
[58] Field of Search ................. 564/246, 247; 514/637

[56] References Cited

U.S. PATENT DOCUMENTS

| | | | |
|---|---|---|---|
| 3,981,911 | 9/1976 | Sletzinger | 260/520 |
| 4,012,524 | 3/1977 | Cragoe | 424/308 |
| 4,070,539 | 1/1978 | Cragoe | 560/56 |
| 4,096,267 | 6/1978 | Cragoe | 424/262 |
| 4,247,715 | 1/1981 | Johnson | 562/462 |
| 4,249,021 | 2/1981 | Cragoe | 562/462 |
| 4,291,050 | 9/1981 | Woltersdorf | 424/278 |
| 4,316,043 | 2/1982 | Cragoe | 560/53 |
| 4,317,922 | 3/1982 | Cragoe | 562/461 |
| 4,334,088 | 6/1982 | Johnson | 562/462 |
| 4,337,354 | 6/1982 | Cragoe | 562/461 |
| 4,356,313 | 10/1982 | Cragoe | 560/53 |
| 4,356,314 | 10/1982 | Cragoe | 560/53 |
| 4,389,417 | 6/1983 | Bourke | 424/317 |
| 4,394,385 | 7/1983 | Cragoe | 424/285 |
| 4,463,208 | 7/1984 | Cragoe | 562/462 |
| 4,465,850 | 8/1984 | Cragoe | 560/53 |
| 4,510,322 | 4/1985 | Blaine | 514/255 |
| 4,579,869 | 4/1986 | Cragoe | 514/561 |
| 4,604,396 | 8/1986 | Cragoe | 514/256 |

FOREIGN PATENT DOCUMENTS

181100 5/1986 European Pat. Off.

OTHER PUBLICATIONS

E. J. Cragoe, Jr. et al., "Agents for the Treatment of Brain Injury. 1. (Aryloxy)Alkanoic Acids," J. Med. Chem., 25, 567–579 (1982).
E. J. Cragoe, Jr. et al., "Agents for the Treatment of Brain Edema. 2. . . . ," J. Med. Chem., 29, 825–841 (1986).
O. W. Woltersdorf, Jr. et al., "(Acylaryloxy)acetic Acid Diuretics. 1. (2-Alkyl- and 2,2-Dialkyl-1-oxo-5-indanyloxy)acetic Acids," J. Med. Chem., 20, 1400–1408 (1977).
R. S. Bourke et al., "Swelling and Ion Uptake in Cat Cerebrocortical Slices: Control by Neurotransmitters and Ion Transport Mechanisms," Neurochem.Res., 8, 5–23 (1983).
E. J. Cragoe, Jr., "Drugs for the Treatment of Traumatic Brain Injury," Medicinal Research Reviews, 1, 271–305 (1987).

*Primary Examiner*—James H. Reamer
*Attorney, Agent, or Firm*—Charles M. Caruso; Hesna J. Pfeiffer

[57] ABSTRACT

This invention relates to novel substituted amidinoalkoxy and amidinoalkylamino indanones and salts thereof. The compounds are useful for the treatment and prevention of injury to the brain and of edema due to head trauma, stroke (particularly ischemic), arrested breathing, cardiac arrest, Reye's syndrome, cerebral thrombosis, cerebral embolism, the neurological problems caused by AIDS, cerebral hemorrhage, cerebral tumors, encephalomyelitis, spinal cord injury, hydrocephalus, post-operative brain injury trauma, edema due to cerebral infections, various brain concussions, and elevated intracranial pressure.

32 Claims, No Drawings

SUBSTITUTED AMIDINOALKOXY AND AMIDINOALKYLAMINO INDANONES AND SALTS THEREOF

BACKGROUND OF THE INVENTION

Trauma to the brain or spinal cord caused by physical forces acting on the skull or spinal column, by ischemic stroke, arrested breathing, cardiac arrest, Reye's syndrome, cerebral thrombosis, cerebral embolism, the neurological problems caused by AIDS, cerebral hemorrhage, encephalomyelitis, hydrocephalus, post-operative brain injury, cerebral infections, various concussions, and elevated intracranial pressure results in edema and swelling of the affected tissues. This is followed by ischemia, hypoxia, necrosis, temporary or permanent brain or spinal cord injury and may result in death. The tissues mainly affected are classified as grey matter, more specifically astroglial cells. The specific therapy currently used for treatment of medical problems described include various kinds of diuretics (particularly osmotic diuretics), steroids (such as, 6-α-methylprednisolone succinate), and barbiturates. The usefulness of these agents is questionable and they are associated with a variety of untoward complications and side effects. See, e.g., E. J. Cragoe, Jr., *Medicinal Research Reviews*, 1,271–305 (1987). Thus, the compounds of this invention comprise a novel and specific treatment of medical problems where no specific therapy is available.

Certain (indanyloxy)alkanoic acid derivatives have been disclosed as useful agents for the treatment and prevention of injury to the brain and spinal cord. See Cragoe et al., *J. Med. Chem.*, 25, 567–579 (1982) and U.S. Pat. Nos. 4,579,869, 4,465,850, 4,463,208, 4,394,385, and 4,389,417. None of these publications, however, discloses the amidinoalkoxy and amidinoalkylamino indanones or salts of the present invention nor suggests their utility for treatment of brain injury or edema. Moreover, the '385 patent discloses indeno[5,4-b]furancarboxylic acids that have a structurally distinct ring system from the compounds of the present invention.

Certain [(tetrahydrofluoren-7-yl)oxy]alkanoic acid derivatives have also been disclosed as useful agents for the treatment and prevention of injury to the brain and spinal cord. See Cragoe et al., *J. Med. Chem.*, 29, 825–841 (1986) and U.S. Pat. Nos. 4,604,396, 4,356,314, 4,356,313, 4,337,354, 4,317,922, and 4,316,043. The compounds disclosed in these publications, however, are carboxylic acid derivatives having a fluorenyl ring nucleus and thus are structurally distinct from the amidinoalkoxy and amidinoalkylamino indanones and salts of the present invention.

The compounds of the invention have the added advantage of being devoid of the pharmacodynamic, toxic or various side effects characteristic of the diuretics, steroids and barbiturates.

SUMMARY OF THE INVENTION

This invention relates to novel substituted amidinoalkoxy and amidinoalkylamino indanones and salts thereof of Formula I that are useful in the treatment and prevention of brain injury and edema.

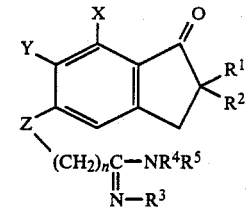

or optical isomers thereof;
or pharmaceutically acceptable acid addition salts thereof;
or a hydrate thereof;
wherein $R^1$ is:
  (a) $C_1$–$C_6$ alkyl;
  (b) $C_3$–$C_7$ cycloalkyl;
  (c) $C_4$–$C_{11}$ (cycloalkyl)alkyl;
  (d) phenyl or phenyl substituted with one or more substituents selected from the group consisting of:
    (i) halogen;
    (ii) $C_1$–$C_6$ alkyl;
    (iii) $C_1$–$C_6$ alkoxy;
    (iv) $C_2$–$C_6$ alkanoyl; and
    (v) hydroxy; or
  (e) phenyl ($C_1$–$C_6$ alkyl) or phenyl ($C_1$–$C_6$ alkyl) substituted in the benzene ring with one or more substituents selected from the group consisting of:
    (i) halogen;
    (ii) $C_1$–$C_6$ alkyl;
    (iii) $C_1$–$C_6$ alkoxy;
    (iv) $C_2$–$C_6$ alkanoyl; and
    (v) hydroxy;
$R^2$ is:
  (a) hydrogen; or
  (b) $C_1$–$C_6$ alkyl;
$R^3$, $R^4$, and $R^5$ are independently:
  (a) hydrogen; or
  (b) $C_1$–$C_6$ alkyl;
X and Y are independently:
  (a) halogen; or
  (b) $C_1$–$C_6$ alkyl;
Z is:
  (a) —O—; or
  (b) —NH—; and
n is an integer of from 1 to 6.

The term "$C_1$–$C_6$ alkyl" refers to straight or branched chain aliphatic hydrocarbon groups having from 1 to 6 carbon atoms, also referred to as lower alkyl. Examples of $C_1$–$C_6$ alkyl are methyl, ethyl, propyl, butyl, pentyl, hexyl, and the isomeric forms thereof.

The term "$C_3$–$C_7$ cycloalkyl" refers to saturated monocyclic hydrocarbon groups having from 3 to 7 carbon atoms in the ring. Examples of $C_3$–$C_7$ cycloalkyl are cyclopropyl, cyclobutyl, cyclopentyl, cyclohexyl, and cycloheptyl.

The term "$C_4$–$C_{11}$ (cycloalkyl)alkyl" refers to straight or branched chain alkyl groups bearing a cycloalkyl group such that the total number of carbon atoms ranges from 4 to 11. Examples of $C_4$–$C_{11}$ (cycloalkyl)alkyl are cyclopropylmethyl, 2-cyclopropylethyl, 3-cyclopropylpropyl, cyclobutylmethyl, 2-cyclobutylethyl cyclopentylmethyl, 2-cyclopentylethyl cyclohexylmethyl, 2-cyclohexylethyl, cycloheptylmethyl, 2-cycloheptylethyl, and the like, and the isomeric forms thereof.

The term "$C_1$-$C_6$ alkoxy" refers to straight or branched chain alkyl oxy groups having from 1 to 6 carbon atoms. Examples of $C_1$-$C_6$ alkoxy are methoxy, ethoxy, propoxy, butoxy, pentyloxy, hexyloxy, and the isomeric forms thereof.

The term "$C_2$-$C_6$ alkanoyl" refers to straight or branched chain alkanoyl groups having from 2 to 6 carbon atoms. Examples of $C_2$-$C_6$ alkanoyl are acetyl, propanoyl, butanoyl, pentanoyl, hexanoyl, and the isomeric forms thereof.

Examples of halogen are fluorine, chlorine, bromine, and iodine.

The term "pharmaceutically acceptable acid addition salt" refers to a salt prepared by contacting a compound of Formula I with an inorganic or organic acid whose anion is generally considered suitable for human consumption. Examples of pharmaceutically acceptable acid addition salts include the acetate, adipate, alginate, aspartate, benzoate, benzenesulfonate, bisulfate, butyrate, citrate, camphorate, camphorsulfonate, cyclopentanepropionate, dodecylsulfate, ethanesulfonate, fumarate, glucoheptanoate, gluconate, glycerophosphate, heptanoate, hexanoate, hydrochloride, hydrobromide, hydroiodide, 2-hydroxyethanesulfonate, lactate, malate, maleate, methanesulfonate, 2-naphthalenesulfonate, nicotinate, pamoate, pectinate, 3-phenylpropionate, phosphate, pivalate, propionate, succinate, sulfate, tartrate, thiocyanate, tosylate, and undecanoate salts.

When the substituents $R^1$ and $R^2$ are different, the 2-position of the indanone ring system is asymmetric and the compounds of this invention of Formula I are racemic. One skilled in the art would understand that compounds of Formula I or their precursors could be resolved into enantiomeric components, which may vary somewhat as to desirable activity or toxicity. One skilled in the art could readily determine the most desirable isomeric composition. It is understood that this invention encompasses the racemic mixtures and the enantiomers.

Although the structure shown for Formula I indicates one tautomeric form for the amidino group, it is understood that this representation is for convenience only and that the scope of this invention includes as equivalents all tautomeric forms of the compounds of this invention.

It is also understood that the compounds of Formula I may form hydrates or other solvates from the solvents in which they are prepared or from which they are crystallized. These hydrates or other solvates may be used per se or they may be dehydrated or desolvated by heating (for example, at about 70° C. to 100° C.) in vacuo.

Although this invention primarily involves novel compounds of Formula I, it also includes derivatives such as oximes, hydrazones, and the like. Additionally, this invention includes pharmaceutical compositions in unit dosage forms containing a pharmaceutical carrier and a pharmaceutically effective amount of a compound of Formula I (as racemate or as an enantiomer) for treating or preventing brain injury and edema. The method of treating a person with brain injury by administering said compounds or said pharmaceutical compositions is also part of this invention.

DESCRIPTION OF THE INVENTION

The compounds of this invention may be prepared by the methods illustrated in the following Scheme A. Unless otherwise specified, the various substituents are defined as for Formula I, above. Scheme A illustrates a method for preparing compounds of this invention from 2-substituted hydroxyindanones aminoindanones of Formula II, which can be prepared using methods known in the art. For hydroxyindanones (wherein Z is —O—), see, for example, Cragoe et al., *J. Med. Chem.*, 25, 567-579 (1982), and Woltersdorf et al., *J. Med Chem.*, 20, 1400-1408 (1977); for aminoindanones (wherein Z is —NH—), see, for example, U.S. Pat. No. 4,579,869.

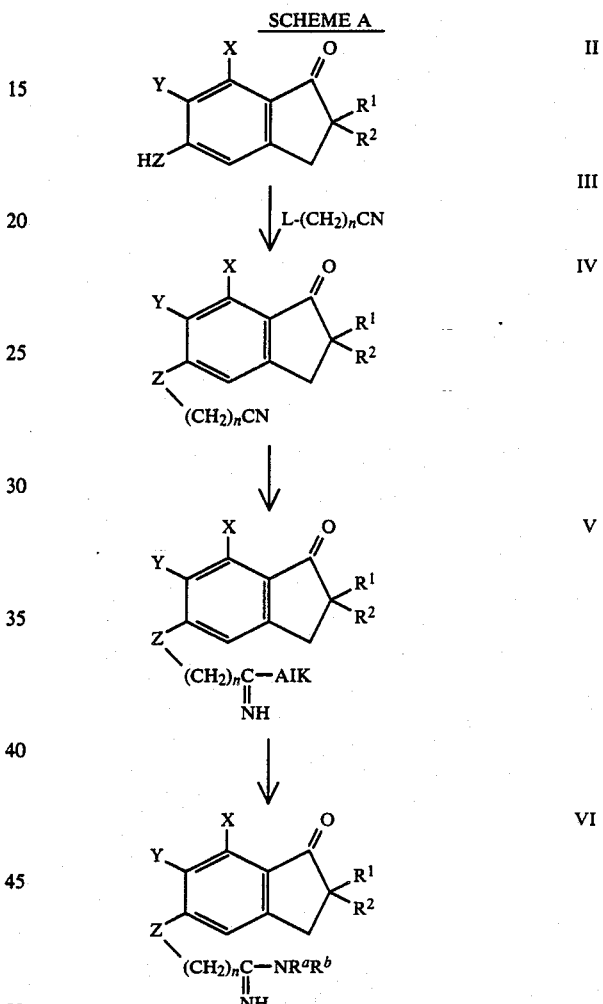

Compounds of Formula II react under suitably basic conditions in a suitable organic solvent with a suitable omega-substituted alkanenitrile of Formula III to form cyanoalkyl intermediates of Formula IV. Suitable omega-substituted alkanenitriles are compounds in which the leaving group L is sufficiently labile to permit the desired reaction to take place. For example, L may be halogen, such as bromine, chloride, or iodine; alkanesulfonate, such as methanesulfonate; and other such leaving groups known in the art. A preferred leaving group L is halogen, preferably chlorine or bromine.

Suitable organic solvents are organic liquids in which reactants may be dissolved or suspended but which are otherwise chemically inert. Examples of suitable organic solvents include ketones, such as acetone, methyl ethyl ketone, and the like; alkanols, such as methanol, ethanol, propanol, isopropyl alcohol, and the like; alkanes and cycloalkanes; ethers and cyclic ethers, such as diethyl ether, tetrahydrofuran, tetrahydropyran, and the like; aromatic hydrocarbons, such as benzene, toluene, and the like; N,N-disubstituted amides, such as dimethylformamide, dimethylacetamide, and the like; N-substituted lactams, such as N-methylpyrrolidinone, N-methylpiperidinone, and the like; and other solvents known in the art. A preferred solvent is acetone.

Suitably basic conditions are achieved by adding a base that facilitates the reaction of a compound of Formula II with the alkanenitrile of Formula III but that does not itself form significant quantities of byproducts by reaction with other chemical reagents or reaction products. For example, a suitable base for reactions of hydroxyindanones (that is, Formula II in which Z is —O—) is a base that can generate a sufficient phenoxide concentration for the reaction to occur readily. Examples of such bases include alkali metal carbonates, such as lithium, sodium, or potassium carbonate; alkali metal alkoxides, such as sodium methoxide, sodium ethoxide, or potassium t-butoxide; alkali metal alkyls, such as n-butyllithium and t-butyllithium; and other such bases known in the art. A suitable base for reactions of aminoindanones (that is, Formula II in which Z is —NH—) is a base that can absorb hydrogen ions generated during the reaction preferentially to the basic aniline-like amino nitrogen atom. In general, such bases need not be so strongly basic as those for reaction of corresponding phenolic indanones. Examples of such bases include, in addition to bases listed above, alkali metal bicarbonates, such as lithium, sodium, or potassium bicarbonate; and other such bases known in the art. The particular base used may depend somewhat on the solvent used. For example, a preferred base-solvent combination is an alkali metal carbonate, preferably sodium carbonate, in a ketone, preferably acetone. As is well known in the art, alkylations analogous to the reaction used to convert compounds of Formula II to compounds of Formula III are facilitated by adding small quantities of iodide ions to the reaction mixture. Thus, potassium iodide has been found useful in the reaction process described above.

Cyanoalkyl intermediates of Formula IV may be converted by any of several methods known in the art to amidino compounds of Formula I of this invention. The remaining steps shown in Scheme A illustrate a method that involves the intermediacy of an imidic ester of Formula V. The preferred general method involves alkanolysis of the cyano group under strongly basic conditions. For example, reaction of a compound IV with an alkali metal alkoxide of the formula M$^+$ $^-$OAlk (where M$^{30}$ is an alkali metal ion and $^-$OAlk represents an alkoxide ion of about 1 to 8 carbon atoms) forms a compound of Formula V. Although many solvents known in the art may be suitable, a convenient and preferred solvent is the alkanol of formula HOAlk, which allows use of only a catalytic amount of the corresponding alkoxide. Furthermore, the alkoxide may be generated in situ by adding an alkali metal to the alkanol. One skilled in the art could readily envision other methods for performing the alkanolysis. In general, the imidic esters are not isolated but are converted in situ to amidines or salts thereof of this invention.

Reaction of imidic esters of Formula V with a salt of ammonia or an amine of the formula NHR$^a$R$^b$.HB (wherein R$^a$ and R$^b$ independently represent hydrogen or C$_1$–C$_6$ alkyl and B represents a pharmaceutically acceptable anion), preferably under slightly acidic conditions, yields salts of amidino compounds of Formula VI. Slightly acidic conditions facilitate the conversion of the alkoxy group to the corresponding alkanol HOAlk as reaction proceeds. Suitable acidity can be produced by using ammonium or amine salts of a strong acid, such as hydrochloric acid, sulfuric acid, trifluoroacetic acid, and the like. A preferred salt is ammonium chloride or an amine hydrochloride of the formula HNR$^a$R$^b$.HCl. It should be noted that the amidino group exists in tautomeric forms. Thus, R$^a$ and R$^b$ may be equivalent to R$^4$ and R$^5$ of Formula I or, if one of R$^a$ and R$^b$ is hydrogen, to R$^3$ of Formula I. Where compounds of Formula VI are further alkylated using methods known in the art, compounds of Formula I in which R$^3$, R$^4$, and R$^5$ are all independently C$_1$–C$_6$ alkyl may be formed. It would be apparent to one skilled in the art that all combinations of R$^3$, R$^4$, and R$^5$ as hydrogen or C$_1$–C$_6$ alkyl could be prepared using suitable methods known in the art. One skilled in the art would also readily understand that compounds of Formula II could be converted directly to compounds of Formula I by reaction with amidinoalkyl compounds of the formula

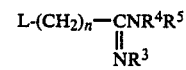

wherein L is a suitably chosen leaving group.

It should be noted that salts of compounds of Formula I can be converted to the free amidine base forms by treatment with a suitable base in a suitable solvent. Suitable bases include alkali metal carbonates, such as lithium, sodium, or potassium carbonate; alkali metal hydroxides, such as lithium, sodium, or potassium hydroxide; alkali metal alkoxides, such as sodium methoxide, sodium ethoxide, or potassium t-butoxide; and other such bases known in the art. Suitable solvents include water (for which alkali metal alkoxides are unsuitable bases) and various alkanols, such as methanol, ethanol, and the like. The resulting free amidine may be converted to different salts by reaction with appropriate inorganic or organic acids whose anions are generally considered suitable for human consumption. Such salts may also be prepared from the free amidine or from other salts by ion exchange methods known to those skilled in the art.

It is to be recognized that certain compounds of Formula I possess an asymmetric carbon atom (the 2-position of the indanone ring system) and therefore the compounds of the invention are racemates which consist of two enantiomers. These enantiomers may possess markedly different biological properties, thus it is advantageous to separate the enantiomers and use them in their pure form. The optically pure compounds of Formula I can be prepared from optically pure precursors of Formula II. Alternatively, the compounds of Formula I can be resolved to their pure enantiomers by one or more of several classical examples. For example, compounds of Formula I may be resolved by forming a salt of the reacemic mixture with an optically active acid such as (+) or (−)-malic acid, (+) or (−)-dibenzoyltartaric acid, (+) or (−)-α-methoxy-α-(triflouromethyl)phenylacetic acid, (+) or (−)-tartaric acid, d- or l-10-camphorsulforic acid, d- or l-α-bromo-camphor-π-sulphonic acid, and the like, in a suitable solvent such as methanol, ethanol, isopropyl alcohol, benzene, acetonitrile, nitromethane, acetone, and the like. There is formed in the solution two diastereomeric salts, one of which is usually less soluble in the solvent than the other. Repetitive recrystallization of the crystalline salt generally affords a pure diastereomeric salt from which is obtained the desired pure enantiomer. The optically pure enantiomer of the compound of Formula I is obtained by reaction of the salt with a base, isolation by filtration, and recrystallization of the optically pure antipode.

The other optically pure antipode may generally be obtained by using a different acid to form the diastereomeric salt. It is of advantage to isolate the partially resolved base from the filtrates of the purification of the first diastereomeric salt and to further purify this substance through the use of another optically active acid. It is especially advantageous to use an optically active acid for the isolation of the second enantiomer which is the antipode of the acid used for the isolation of the first enantiomer. For example, if (—)-malic acid was used first, then (+)-malic acid is used for the isolation of the second (remaining) enantiomer.

The preferred embodiments of this invention include compounds of the formula

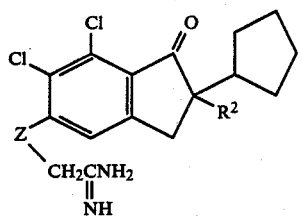

VII and optical isomers thereof; and pharmaceutically acceptable acid addition salts thereof; and hydrates thereof; wherein $R^2$ is $C_1$-$C_6$ alkyl, and Z is —O— or —NH—.

More preferred embodiments of this invention include compounds of the formula

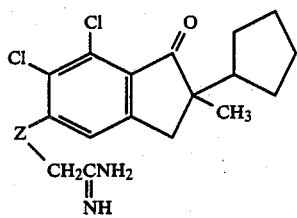

VIII and optical isomers thereof; and the hydrochloride salts thereof; and hydrates thereof; wherein Z is —O— or —NH—.

Intrinsic activity in inhibiting the swelling of brain tissue was demonstrated in an in vitro cerebrocortical cat brain slice assay that simulates the edema seen in traumatic brain injury. See, e.g., Bourke et al., *Neurochem. Res.*, 8, 5 (1983), and Cragoe et al., *J. Med. Chem.*, 25, 567 (1982).

In Vitro Cerebrocortical Cat Brain Tissue Slice Assay

Adult cats of 2-3 kg body weight were employed in tissue slice studies. Prior to sacrifice, the animals were anesthetized with ketamine hydrochloride, 10 mg/kg intramuscularly. Eight (three control, five experimental) pial surface cerebrocortical tissue slices (0.5 mm thick; approximately 150 mg initial fresh weight) were cut successively with a calibrated Stadie-Riggs fresh tissue microtome without moistening and weighed successively on a torsion balance. During the slice preparation all operations except weighing were confined to a humid chamber. Each slice was rapidly placed in an individual Warburg flask containing 2 ml of incubation medium at room temperature. The basic composition of the incubation media was as follows: glucose, 10 mM; $CaCl_2$, 1.3 mM; $MgSO_4$, 1.2 mM; $KHSO_4$, 1.2 mM; HEPES (N-2-hydroxyethylpiperazine-N'-2-ethanesulfonic acid, titrated with NaOH to pH 7.4), 20 mM. Except when adding $HCO_3^-$, the osmolarity of the media was maintained isosmotic (approximately 285 mOsm/L) by reciprocal changes of $Na^+$ or $K^+$ to achieve a concentration of $K^+$ of 27 mM. The basic medium was saturated with oxygen by bubbling pure oxygen through the solution for 30 minutes before use. When added, sodium bicarbonate or triethylammonium bicarbonate was initially present in the sidearm of each flask at an initial concentration of 50 mM in 0.5 ml of complete medium. Nonbicarbonate control slices were incubated at 37° C. in 2.5 ml of basic medium for 60 minutes. Bicarbonate control slices were similarly incubated for an initial 20 minutes at 37° C. in 2.0 ml of basic medium to which was added from the sidearm an additional 0.5 ml of incubation medium containing 50 mM $HCO_3^-$, which, after mixing, resulted in a $HCO_3^-$ concentration of 10 mM and a total volume in 2.5 ml. The incubation is continued for an additional 40 minutes. The various compounds tested were typically dissolved as the hydrochloride salts in water. When only the free bases were available, the hydrochloride salts were formed by treating the free base with a molar equivalent of hydrochloric acid and diluting to the appropriate concentrations. Just prior to incubation, all flasks containing $HCO_3^-$ were gassed for 5 minutes with 2.5% $CO_2$/97.5% $O_2$ instead of 100% $O_2$.

Following the 60-minute incubation period, tissue slices were separated from incubation medium by filtration, reweighed, and homogenized in 1N $HClO_4$ (10% w/v) for electrolyte analysis. The tissue content of ion is expressed in micromoles per gram initial preswelling fresh weight. Control slice swelling is expressed as microliters per gram initial preswelling fresh weight. The effectiveness of an inhibitor at a given concentration was measured by the amount of $HCO_3^-$-stimulated swelling that occurred in its presence, computed as a percent of the maximum possible and is reported as an $IC_{50}$. (See, e.g., Table I (Example 10)). Tissue and media $Na^+$ and $K^+$ levels were determined by emission flame photometry with $Li^+$ internal standard; $Cl^-$ levels were determined by amperometric titration. Tissue viability during incubation is monitored by manometry.

Inasmuch as there are a variety of symptoms and severity associated with grey matter edema, particularly when it is caused by head trauma, stroke, cerebral hemorrhage or embolism, post-operative brain surgery trauma, spinal cord injury, cerebral infections, various brain concussions, elevated intracranial pressure, arrested breathing, cardiac arrest, Reye's syndrome cerebral tumors, encephalomeylitis, hydrocephalus and neurological problem caused by AIDS, the precise treatment is left to the practioner. Generally, candidates for treatment will be indicated by the results of the patient's initial general neurological status, findings on specific clinical brain stem functions and findings on computerized axial tomography (CAT), nuclear magnetic resonance (NMR) or positron emission tomography (PET) scans of the brain. The sum of the neurological evaluation is presented in the Glascow Coma Score or similar scoring system. Such a scoring system is often valuable in selecting the patients who are candidates for therapy of this kind.

The compounds of this invention can be administered by a variety of established methods, including intravenously, intramuscularly, subcutaneously, or orally. The parenteral route, particularly the intravenous route of administration, is preferred, especially for the very ill and comatose patient. Another advantage of the intravenous route of administration is the speed with which therapeutic brain levels of the drug are achieved. It is of paramount importance in brain injury of the type described to initiate therapy as rapidly as possible and to maintain it through the critical time periods. For this purpose, the intravenous administration of drugs of the type of Formula I in the form of their salts is superior.

A recommended dosage range for treatment is expected to be from 0.05 mg/kg to 50 mg/kg of body weight as a single dose, preferably from 0.5 mg/kg to 20 mg/kg. An alternative to the single dose schedule is to administer a primary loading dose followed by a sustaining dose of half to equal the primary dose, every 4 to 24 hours. When this multiple dose schedule is used the dosage range may be higher than that of the single dose method. Another alternative is to administer an ascending dose sequence of an initial dose followed by a sustaining dose of 1½ to 2 times the initial dose every 4 to 24 hours. For example, three intravenous doses of 4, 8, 12, or 16 mg/kg of body weight can be given at 6 hour intervals. If necessary, four additional doses of 4, 8, 12, or 16 mg/kg of body weight can be given at 12 hour intervals. Another effective dose regimen consists of a continuous intravenous infusion of from 0.05 mg/kg/hr to 3.0 mg/kg/hr. Of course, other dosing schedules and amounts are possible.

One aspect of this invention is the treatment of persons with grey matter edema by concomitant administration of a compound of Formula I and an antiinflammatory steroid. These steroids are of some, albeit limited, use in control of white matter edema associated with ischemic stroke and head injury. Steroid therapy is given according to established practice as a supplement to the compound of Formula I. Similarly, a barbiturate may be administered as a supplement to treatment with a compound of Formula I.

The compounds of this invention are utilized by formulating a pharmaceutically effective amount of at least one compound of Formula I in a pharmaceutical composition such as tablet, capsule, or elixir for oral administration. Sterile solutions or suspensions can be used for parenteral administration. A compound or mixture of compounds of Formula I is compounded with a nontoxic pharmaceutically acceptable vehicle, carrier, excipient, binder, preservative, stabilizer, flavor, and the like, in a dosage form as called for by accepted pharmaceutical practice.

Illustrative of the adjuvants which may be incorporated in tablets, capsules, and the like are the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise enhance the pharmaceutical elegance of the preparation. For instance, tablets may be coated with shellac, sugar, or the like. A syrup or elixir may contain the active compound, sucrose as a sweetening agent, methyl and propyl parabens as preservatives, a dye, and a flavoring such as cherry or orange flavor.

Sterile compositions for injection or infusion can be formulated according to conventional pharmaceutical practice by dissolving the active substance in a conventional vehicle such as water, saline, or dextrose solution by forming a soluble salt in water using an appropriate acid, such as a pharmaceutically acceptable carboxylic acids or mineral acids. Alternatively, a suspension of the active substance in a naturally occurring vegetable oil like sesame oil, coconut oil, peanut oil, cottonseed oil, and the like, or a synthetic fatty vehicle like ethyl oleate or the like may be formulated for injection or infusion. Buffer, preservatives, antioxidants, and the like can be incorporated as required.

The following Examples are included to illustrate the preparation of representative compounds of Formula I. It is intended that the specification and examples be considered as exemplary only, with the true scope and spirit of the invention being indicated by the following claims. All temperatures in the examples are in Celsius unless otherwise indicated.

DESCRIPTION OF THE PREFERRED EMBODIMENTS

EXAMPLE 1

[(2-Cyclopentyl-6,7-dichloro-2,3-dihydro-2-methyl-1-oxo-1H-inden-5-yl)oxy]acetonitrile

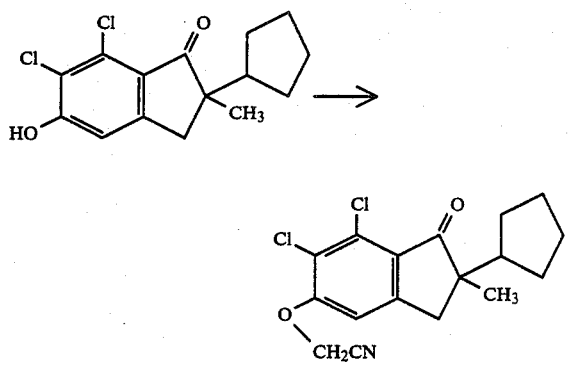

A mixture of 6,7-dichloro-2-cyclopentyl-5-hydroxy-2-methyl-2,3-dihydro-1H-inden-1-one (9.0 g, 30 mmole), chloroacetonitrile (2.5 g, 33 mmole), potassium carbonate (4.15 g), and potassium iodide (0.5 g) in acetone (150 ml) was stirred at reflux for 19 hours. Concentration to dryness in vacuo yielded an oil that crystallized upon trituration with water. Recrystallization from benzene-cyclohexane (ca. 1:3 by volume) gave the title compound (8.5 g), m.p. 129°–131°.

EXAMPLE 2

[(2-Cyclopentyl-6,7-dichloro-2,3-dihydro-2-methyl-1-oxo-1H-inden-5-yl)oxy]ethanimidamide hydrochloride hemihydrate

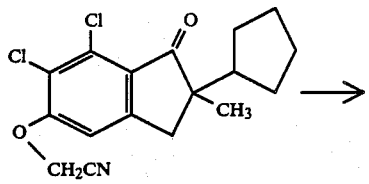

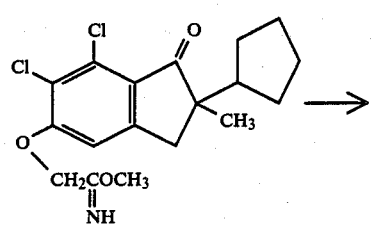

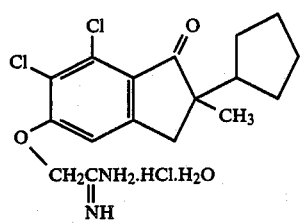

To a suspension of [(2-cyclopentyl-6,7-dichloro-2,3-dihydro-2-methyl-1-oxo-1H-inden-5-yl)oxy]acetonitrile (3.88 g, 10 mmole; see Example 1) in methanol (50 ml) was added sodium metal (0.1 g, 4 mg-atom), and the mixture was stirred for one hour. Ammonium chloride (0.6 g, 11 mmole) was added and the mixture was stirred overnight. The mixture was concentrated to dryness in vacuo, and the resultant residue was triturated with boiling benzene, then collected by filtration. The solid was dissolved in a minimum amount of dimethylformamide and filtered. The filtrate was diluted with diethyl ether (100 ml), giving an oil from which the ether supernatant was removed by decanting. Trituration with warm benzene gave a solid. The ether than was removed by decanting produced an additional quantity of the oil, which solidified on standing. The solids were combined and dissolved in boiling dioxane (50 ml). The cloudy solution was decolorized with charcoal, filtered, and diluted with benzene to yield a white solid. Drying at 80° at 1 mm Hg pressure produced the title compound (ca. 1.7 g) as an analytically pure solid.

Analysis. Calc'd for $C_{17}H_{20}N_2O_2Cl_2 \cdot HCl \cdot \frac{1}{2}H_2O$: C, 50.95; H, 5.53; N, 6.99; Cl, 26.54. Found: C, 50.53, 50.38; H, 5.37, 5.35; N, 6.96, 6.86; Cl, 26.45.

EXAMPLE 3

[(2-Cyclopentyl-6,7-dichloro-2,3-dihydro-2-methyl-1-oxo-1H-inden-5-yl)amino]acetonitrile

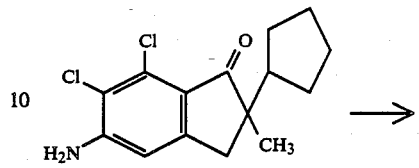

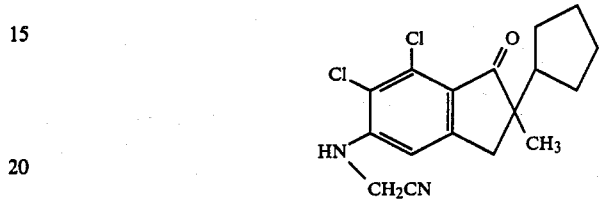

The title compound was prepared by the method of Example 1 using 5-amino-2-cyclopentyl-6,7-dichloro-2-methyl-2,3-dihydro-1H-inden-1-one (8.9 g, 30 mmole) instead of 6,7-dichloro-2-cyclopentyl-5-hydroxy-2-methyl-2,3-dihydro-1H-inden-1-one. Concentration to dryness and trituration of the residue with water gave the title compound.

EXAMPLE 4

[(2-Cyclopentyl-6,7-dichloro-2,3-dihydro-2-methyl-1-oxo-1H-inden-5-yl)amino]ethanimidamide hydrochloride

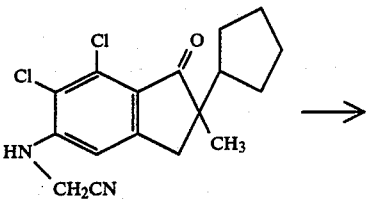

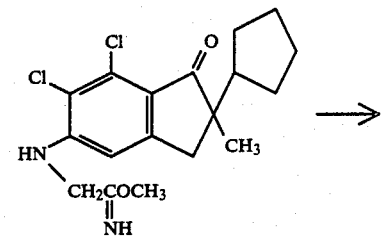

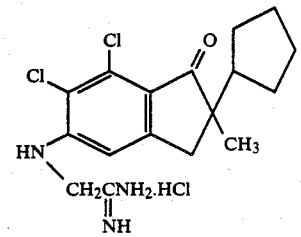

Sodium metal (0.1 g, 4 mg-atom) was added to methanol (50 ml) to form a solution of sodium methoxide. To this solution was added [(2-cyclopentyl-6,7-dichloro- 2,3-dihydro-2-methyl-1-oxo-1H-inden-5-yl)amino]acetonitrile (3.37 g, 10 mmole; see Example 3), and the mixture was stirred for one hour at room temperature. Ammonium chloride (0.6 g, 11 mmole) was added and the mixture was stirred for 16 hours. The mixture was concentrated to dryness in vacuo, and the resultant residue was triturated with boiling benzene, then collected by filtration. The solid was dissolved in ethanol and the resultant solution was diluted with diethyl ether. The precipitate that formed was collected by filtration and dried to yield the title compound.

EXAMPLE 5

(+)[(2-Cyclopentyl-6,7-dichloro-2,3-dihydro-2-methyl-1-oxo-1H-inden-5-yl)oxy]acetonitrile

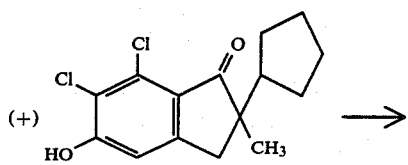

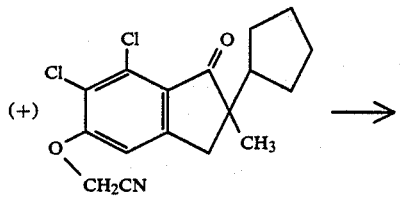

A mixture of (+) 6,7-dichloro-2-cyclopentyl-5-hydroxy-2-methyl-2,3-dihydro-1H-inden-1-one (3.29 g, 11 mmole), chloroacetonitrile (1.25 g, 16.5 mmole), and potassium carbonate (3.04 g) in dimethylformamide (30 ml) was stirred at 60°–65° for three hours. The reaction mixture was poured into water and extracted with dichloromethane. The organic layer was washed with water, dried over magnesium sulfate, and concentrated in vacuo to give the title compound as an oil (3.8 g).

EXAMPLE 6

(+)[(2-Cyclopentyl-6,7-dichloro-2,3-dihydro-2-methyl-1-oxo-1H-inden-5-yl)oxy]ethanimidamide hydrochloride ¼ hydrate

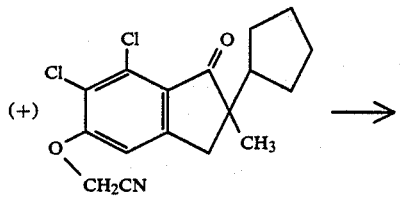

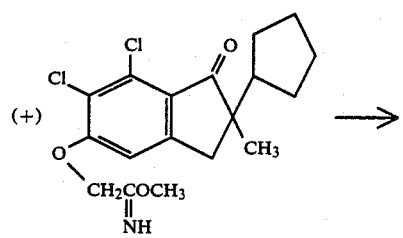

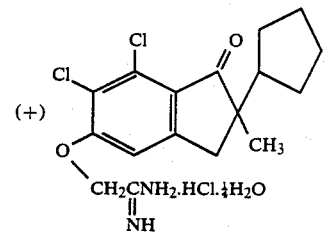

The title (+) enantiomer was prepared by the method of Example 2 using (+)[(2-cyclopentyl-6,7-dichloro-2,3-dihydro-2-methyl-1-oxo-1H-inden-5-yl)oxy]acetonitrile (3.55 g, 10 mmole) instead of the unresolved compound, with appropriate adjustment of quantities. The title compound was isolated as the analytically pure ¼ hydrate.

Analysis. Calc'd for $C_{17}H_{20}N_2O_2Cl_2 \cdot HCl \cdot \frac{1}{4}H_2O$: C, 51.53; H, 5.47; N, 7.07. Found: C, 51.56; H, 5.45; N, 6.84.

EXAMPLE 7

(−)[(2-Cyclopentyl-6,7-dichloro-2,3-dihydro-2-methyl-1-oxo-1H-inden-5-yl)oxy]ethanimidamide hydrochloride ¼ hydrate

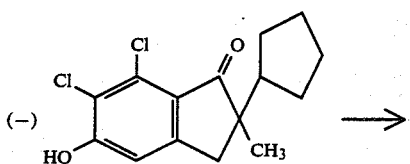

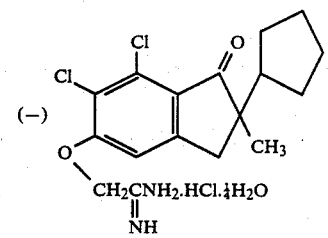

The title (−) enantiomer was prepared by the methods of Examples 5 and 6 using the corresponding (−) enantiomers. The title compound was isolated as the ¼ hydrate.

EXAMPLE 8

4-[(2-Cyclopentyl-6,7-dichloro-2,3-dihydro-2-methyl-1-oxo-1H-inden-5-yl)oxy]butanenitrile

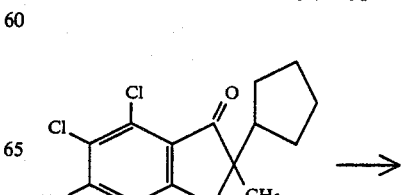

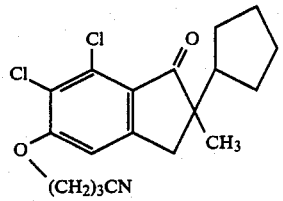

A mixture of 6,7-dichloro-2-cyclopentyl-5-hydroxy-2-methyl-2,3-dihydro-1H-inden-1-one (6.0 g, 20 mmole), 4-bromobutanenitrile (3.28 g, 22 mmole), and potassium carbonate (3.1 g, 22 mmole) in dimethylformamide (50 ml) was stirred at 60°–65° for four hours. The reaction mixture was poured into water and extracted with diethyl ether. The organic layer was washed successively with water and brine, dried over magnesium sulfate, and concentrated in vacuo to a solid residue (4.7 g). Recrystallization from butyl chloride-hexane afforded the analytically pure title compound, m.p. ca. 112°.

Analysis. Calc'd For $C_{19}H_{21}NO_2Cl_2$: C, 62.30; H, 5.78; N, 3.82. Found: C, 62.57; H, 5.81; N, 3.73.

EXAMPLE 9

4-[(2-Cyclopentyl-6,7-dichloro-2,3-dihydro-2-methyl-1-oxo-1H-inden-5-yl)oxy]butanimidamide hydrochloride

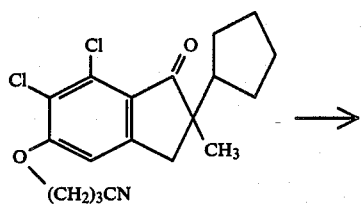

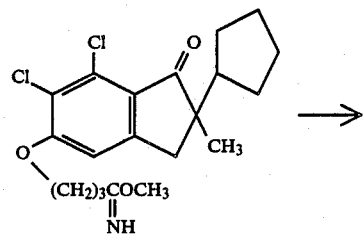

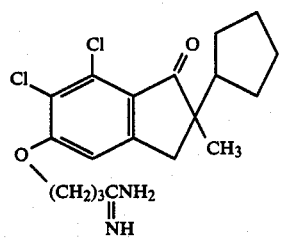

A solution of 4-[2-cyclopentyl-6,7 dichloro-2,3-dihydro-2-methyl-1-oxo-1H-inden-5-yl)oxy]butanenitrile (3.66 g, 10 mmole; see Example 8) and ethanol (0.65 ml) in chloroform (40 ml) was cooled in ice, then saturated with hydrogen chloride gas and kept at 0° for 18 hours. The mixture was slowly added to excess 10N aqueous sodium hydroxide. The organic layer was washed with water, dried over potassium carbonate, and concentrated in vacuo to an oil. To a solution of the oil in a mixture of ethanol (30 ml) and water (5 ml) was added ammonium chloride (0.7 g). After four hours of stirring, the mixture was filtered and concentrated in vacuo. Trituration with acetone and recrystallization from ethanol-diethyl ether gave the analytically pure title compound, m.p. 218°–220°.

Analysis. Calc'd For $C_{19}H_{24}N_2O_2Cl_2 \cdot HCl$: C, 54.36; H, 6.00; N, 6.67. Found: C, 54.33; H, 6.10; N, 6.84.

EXAMPLE 10

Biological results

TABLE I

| In vitro Cerebrocortical Cat Brain Tissue Slice Assay | |
|---|---|
| Compound (Example No.) | $IC_{50}$ (nM) |
| 2 | 10 |
| 6 | 100 |
| 7 | 5 |

What is claimed is:

1. A compound having the formula:

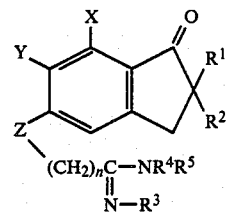

or optical isomers thereof;
or pharmaceutically acceptable acid addition salts thereof;
or a hydrate thereof;
wherein $R^1$ is:
  (a) $C_1$–$C_6$ alkyl;
  (b) $C_3$–$C_7$ cycloalkyl;
  (c) $C_4$–$C_{11}$ (cycloalkyl)alkyl;
  (d) phenyl or phenyl substituted with one or more substituents selected from the group consisting of:
    (i) halogen;
    (ii) $C_1$–$C_6$ alkyl;
    (iii) $C_2$–$C_6$ alkoxy;
    (iv) $C_2$–$C_6$ alkanoyl; and
    (v) hydroxy; or
  (e) phenyl($C_1$–$C_6$ alkyl) or phenyl($C_1$–$C_6$ alkyl) substituted in the benzene ring with one or more substituents selected from the group consisting of:
    (i) halogen;
    (ii) $C_1$–$C_6$ alkyl;
    (iii) $C_2$–$C_6$ alkoxy;
    (iv) $C_2$–$C_6$ alkanoyl; and
    (v) hydroxy;
$R^2$ is:
  (a) hydrogen; or
  (b) $C_1$–$C_6$ alkyl;
$R^3$, $R^4$, and $R^5$ are independently:
  (a) hydrogen; or
  (b) $C_1$–$C_6$ alkyl;
X and Y are independently:
  (a) halogen; or
  (b) $C_1$–$C_6$ alkyl;
Z is:
  (a) —O—; or
  (b) —NH—; and n is an integer of from 1 to 6.

2. A compound according to claim 1 having the formula

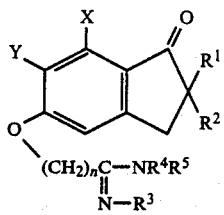

or optical isomers thereof;
or pharmaceutically acceptable acid addition salts thereof;
or a hydrate thereof;
wherein $R^1$ is:
  (a) $C_1$–$C_6$ alkyl;
  (b) $C_3$–$C_7$ cycloalkyl;
  (c) $C_4$–$C_{11}$ (cycloalkyl)alkyl;
  (d) phenyl or phenyl substituted with one or more substituents selected from the group consisting of:
    (i) halogen;
    (ii) $C_1$–$C_6$ alkyl;
    (iii) $C_2$–$C_6$ alkoxy;
    (iv) $C_2$–$C_6$ alkanoyl; and
    (v) hydroxy; or
  (e) phenyl($C_1$–$C_6$ alkyl) or phenyl($C_1$–$C_6$ alkyl) substituted in the benzene ring with one or more substituents selected from the group consisting of:
    (i) halogen;
    (ii) $C_1$–$C_6$ alkyl;
    (iii) $C_2$–$C_6$ alkoxy;
    (iv) $C_2$–$C_6$ alkanoyl; and
    (v) hydroxy;
$R^2$ is:
  (a) hydrogen; or
  (b) $C_1$–$C_6$ alkyl;
$R^3$, $R^4$, and $R^5$ are independently:
  (a) hydrogen; or
  (b) $C_1$–$C_6$ alkyl;
X and Y are independently:
  (a) halogen; or
  (b) $C_1$–$C_6$ alkyl; and
n is an integer of from 1 to 6.

3. A compound according to claim 2 wherein X and Y are independently halogen.

4. A compound according to claim 3 wherein the halogen in chlorine.

5. A compound according to claim 2 wherein $R^1$ is $C_3$–$C_7$ cycloalkyl.

6. A compound according to claim 5 wherein $R^1$ is cyclopentyl.

7. A compound according to claim 2 wherein $R^3$, $R^4$, and $R^5$ are each hydrogen.

8. A compound according to claim 2 having the formula

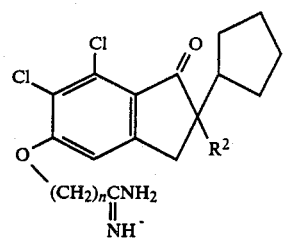

or optical isomers thereof;
or a pharmaceutically acceptable acid addition salt thereof;
or a hydrate thereof;
wherein $R^2$ is:
  (a) hydrogen; or
  (b) $C_1$–$C_6$ alkyl; and
n is an integer of from 1 to 6.

9. A compound according to claim 8 wherein $R^2$ is $C_1$–$C_6$ alkyl.

10. A compound according to claim 8 wherein the pharmaceutically acceptable acid addition salt is a hydrochloride salt.

11. A compound according to claim 8 having the formula

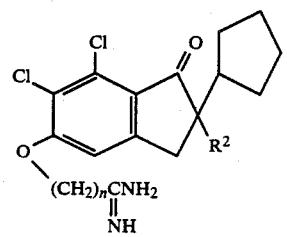

or optical isomers thereof;
or a hydrochloride salt thereof;
or a hydrate thereof;
wherein $R^2$ is $C_1$–$C_6$ alkyl and n is an integer of from 1 to 6.

12. A compound according to claim 11 which is [(2-cyclopentyl-6,7-dichloro-2,3-dihydro-2-methyl-1-oxo-1H-inden-5-yl)oxy]ethanimidamide hydrochloride or a hydrate thereof.

13. A compound according to claim 11 which is (+)[(2-cyclopentyl-6,7-dichloro-2,3-dihydro-2-methyl-1-oxo-1H-inden-5-yl)oxy]ethanimidamide hydrochloride or a hydrate thereof.

14. A compound according to claim 11 which is (−)[(2-cyclopentyl-6,7-dichloro-2,3-dihydro-2-methyl-1-oxo-1H-inden-5-yl)oxy]ethanimidamide hydrochloride or a hydrate thereof.

15. A compound according to claim 11 which is 4-[(2-cyclopentyl-6,7-dichloro-2,3-dihydro-2-methyl-1-oxo-1H-inden-5-yl)oxy]butanimidamide hydrochloride or a hydrate thereof.

16. A compound having the formula

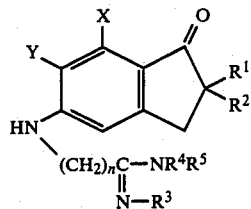

or optical isomer thereof;
or a pharmaceutically acceptable acid addition salt thereof;
or a hydrate thereof;
wherein $R^1$ is:
  (a) $C_1$–$C_6$ alkyl;
  (b) $C_3$–$C_7$ cycloalkyl;
  (c) $C_4$–$C_{11}$ (cycloalkyl)alkyl;
  (d) phenyl or phenyl substituted with one or more substituents selected from the group consisting of:
    (i) halogen;
    (ii) $C_1$–$C_6$ alkyl;
    (iii) $C_2$–$C_6$ alkoxy;
    (iv) $C_2$–$C_6$ alkanoyl; and
    (v) hydroxy; or
  (e) phenyl($C_1$–$C_6$ alkyl) or phenyl($C_1$–$C_6$ alkyl) substituted in the benzene ring with one or more substituents selected from the group consisting of:
    (i) halogen;
    (ii) $C_1$–$C_6$ alkyl;
    (iii) $C_2$–$C_6$ alkoxy;
    (iv) $C_2$–$C_6$ alkanoyl; and
    (v) hydroxy;
$R^2$ is:
  (a) hydrogen; or
  (b) $C_1$–$C_6$ alkyl;
$R^3$, $R^4$, and $R^5$ are independently:
  (a) hydrogen; or
  (b) $C_1$–$C_6$ alkyl;
X and Y are independently:
  (a) halogen; or
  (b) $C_1$–$C_6$ alkyl; and
n is an integer of from 1 to 6.

17. A compound according to claim 16 wherein X and Y are independently halogen.

18. A compound according to claim 17 wherein the halogen is chlorine.

19. A compound according to claim 16 wherein $R^1$ is $C_3$–$C_7$ cycloalkyl.

20. A compound according to claim 19 wherein $R^1$ is cyclopentyl.

21. A compound according to claim 16 wherein $R^3$, $R^4$, and $R^5$ are each hydrogen.

22. A compound according to claim 16 having the formula

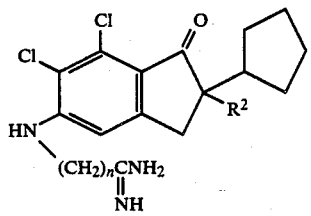

or optical isomers thereof;

or a pharmaceutically acceptable acid addition salt thereof;
or a hydrate thereof;
wherein $R^2$ is:
  (a) hydrogen; or
  (b) $C_1$–$C_6$ alkyl; and
n is an integer of from 1 to 6.

23. A compound according to claim 22 wherein $R^2$ is $C_1$–$C_6$ alkyl.

24. A compound according to claim 22 wherein the pharmaceutically acceptable acid addition salt is a hydrochloride salt.

25. A compound according to claim 22 having the formula

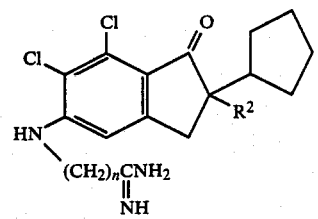

or optical isomers thereof;
or a hydrochloride salt thereof;
or a hydrate thereof;
wherein $R^2$ is $C_1$–$C_6$ alkyl and n is an integer of from 1 to 6.

26. A compound according to claim 25 which is [(2-cyclopentyl-6,7-dichloro-2,3-dihydro-2-methyl-1-oxo-1H-inden-5-yl)amino]ethanimidamide hydrochloride or a hydrate thereof.

27. A pharmaceutical composition useful in the treatment of brain injury and edema comprising a pharmaceutically effective amount of at least one compound according to claim 1, together with one or more non-toxic pharmaceutically acceptable carriers.

28. A pharmaceutical composition according to claim 27 wherein said compound is selected from the group consisting of:
[(2-cyclopentyl-6,7-dichloro-2,3-dihydro-2-methyl-1-oxo-1H-inden-5-yl)oxy]ethanimidamide or an optical isomer thereof or a hydrochloride salt thereof;
4-[(2-cyclopentyl-6,7-dichloro-2,3-dihydro-2-methyl-1-oxo-1H-inden-5-yl)oxy]butanimidamide or a hydrochloride salt thereof; and
[(2-cyclopentyl-6,7-dichloro-2,3-dihydro-2-methyl-1-oxo-1H-inden-5-yl)amino]ethanimidamide or a hydrochloride salt thereof.

29. A method for treating brain injury and edema comprising administering a pharmaceutically effective amount of at least one compound of claim 1 to a patient in need of such treatment.

30. A method according to claim 29 wherein said compound is selected from the group consisting of:
[(2-cyclopentyl-6,7-dichloro-2,3-dihydro-2-methyl-1-oxo-1H-inden-5-yl)oxy]ethanimidamide or an optical isomer thereof or a hydrochloride salt thereof;
4-[(2-cyclopentyl-6,7-dichloro-2,3-dihydro-2-methyl-1-oxo-1H-inden-5-yl)oxy]butanimidamide or a hydrochloride salt thereof; and
[(2-cyclopentyl-6,7-dichloro-2-methyl-1-oxo-1H-inden-5-yl)amino]ethanimidamide or a hydrochloride salt thereof.

31. A method for treating brain injury comprising administering a pharmaceutically effective amount of a pharmaceutical composition of claim 27 to a patient in need of such treatment.

32. A method according to claim 31 wherein the compound of said pharmaceutical composition is selected from the group consisting of:

[(2-cyclopentyl-6,7-dichloro-2,3-dihydro-2-methyl-1-oxo-1H-inden-5-yl)oxy]ethanimidamide or an optical isomer thereof or a hydrochloride salt thereof;

4-[(2-cyclopentyl-6,7-dichloro-2,3-dihydro-2-methyl-1-oxo-1H-inden-5-yl)oxy]butanimidamide or a hydrochloride salt thereof; and

[(2-cyclopentyl-6,7-dichloro-2,3-dihydro-2-methyl-1-oxo-1H-inden-5-yl)amino]ethanimidamide or a hydrochloride salt thereof.

* * * * *